United States Patent
Yeh et al.

(10) Patent No.: US 7,371,910 B2
(45) Date of Patent: May 13, 2008

(54) PROCESS FOR BENZENE ALKYLATION AND TRANSALKYLATION OF POLYALKYLATED AROMATICS OVER IMPROVED ZEOLITE BETA CATALYST

(75) Inventors: Chuen Y. Yeh, Edison, NJ (US); Jinsuo Xu, Hillsborough, NJ (US); Philip J. Angevine, Woodbury, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 593 days.

(21) Appl. No.: 11/000,859

(22) Filed: Dec. 1, 2004

(65) Prior Publication Data

US 2005/0154243 A1    Jul. 14, 2005

Related U.S. Application Data

(63) Continuation-in-part of application No. 10/422,464, filed on Apr. 24, 2003, now Pat. No. 6,844,479, which is a continuation-in-part of application No. 09/981,926, filed on Oct. 17, 2001, now Pat. No. 6,809,055.

(60) Provisional application No. 60/242,110, filed on Oct. 20, 2000.

(51) Int. Cl.
  *C07C 2/64* (2006.01)
(52) U.S. Cl. ........................................ 585/467
(58) Field of Classification Search ............... 585/467
See application file for complete search history.

(56) References Cited

U.S. PATENT DOCUMENTS

| 3,385,906 A | 5/1968 | Kaufman |
| 4,169,111 A | 9/1979 | Wight |
| 4,292,458 A | 9/1981 | Klotz |
| 4,891,458 A | 1/1990 | Innes et al. |
| 5,015,786 A | 5/1991 | Araki et al. |
| 5,160,497 A | 11/1992 | Juguin et al. |
| 6,440,886 B1 | 8/2002 | Gajda et al. |

FOREIGN PATENT DOCUMENTS

| EP | 0 308 097 B1 | 1/1992 |
| EP | 0 847 802 A1 | 6/1998 |
| EP | 0 687 500 B1 | 2/2000 |
| EP | 0 439 632 B2 | 12/2002 |

*Primary Examiner*—Thuan D. Dang
(74) *Attorney, Agent, or Firm*—Dilworth & Barrese, LLP

(57) ABSTRACT

An aromatic alkylation process includes contacting an aromatic compound with an alkylating agent in the presence of a zeolite beta in a reaction zone under alkylation reaction conditions, wherein said zeolite beta is a high performance zeolite beta possessing a ratio of strong acid sites/weak acid sites greater than 1. The high performance zeolite beta is superior to conventional zeolite beta in the aromatics alkylation reaction, such as benzene alkylation with ethylene for ethylbenzene production, and benzene alkylation with propylene for cumene production.

18 Claims, No Drawings

PROCESS FOR BENZENE ALKYLATION AND TRANSALKYLATION OF POLYALKYLATED AROMATICS OVER IMPROVED ZEOLITE BETA CATALYST

CROSS REFERENCE TO RELATED APPLICATIONS

The present application is a continuation-in-part of U.S. patent application Ser. No. 10/422,464 filed Apr. 24, 2003 now U.S. Pat. No. 6,844,479, which is a continuation in part application of U.S. patent application Ser. No. 09/981,926 filed Oct. 17, 2001, now issued as U.S. Pat. No. 6,809,055 B2, which claimed priority to U.S. Provisional application No. 60/242,110, filed Oct. 20, 2000, to which the present application also claims priority. The contents of the aforementioned applications and patent are incorporated by reference herein in their entirety.

BACKGROUND

1. Field of the Invention

The present invention relates to a catalytic process for alkylation of aromatic hydrocarbon compounds.

2. Background of the Art

Alkylation of aromatic compounds with olefins has been used in the production of many important chemicals or petrochemical products or intermediates, such as ethylbenzene for polystyrene polymer, cumene for phenol synthesis, and long chain alkylbenzene for the detergent industry. Generally, catalysts are used in these processes to enable the chemical reaction to occur at milder conditions (e.g. low temperatures and/or low pressures) in addition to make the reaction more selective toward desired products.

In 1965 the preparation of cumene by the reaction of benzene with propylene, using zeolite X or Y as catalyst, was first described [Minachev, Kr. M., et al, Neftekhimiya 5 (1965) 676]. Venuto et al (J. Catal. 5, (1966) 81) subsequently described faujasitic zeolite catalysts for the alkylation of benzene with light olefins. U.S. Pat. No. 4,292,458 describes the use of ZSM-5 type zeolites for alkylating benzene with ethylene. At present, the commercial benzene alkylation processes with ethylene or propylene in liquid phase often use zeolite beta as the alkylation catalyst (e.g. U.S. Pat. No. 4,891,458).

U.S. Pat. No. 5,015,786 describes benzene alkylation with isopropanol catalyzed by zeolite Y.

In U.S. Pat. No. 5,160,497, a dealuminated zeolite Y is used with a molar ratio ranging from 8 to 70 for the alkylation of benzene with propylene and/or isopropanol.

Preparation of monoalkylated aromatic hydrocarbon by the transalkylation of polyalkylated aromatic hydrocarbons with aromatic substrates in which zeolite catalysts with small, medium and large pores are used, are described in U.S. Pat. No. 3,385,906, U.S. Pat. No. 4,169,111 and EP 308,097.

EP 439,632, EP 687,500 and EP 847,802 describe the production of monoalkylated aromatic hydrocarbons from aromatic hydrocarbon substrates, not only by means of alkylation, but also by means of transalkylation and a combined alkylation and transalkylation process, catalyzed by zeolite beta. In particular, reactions described include alkylation of benzene with ethylene or propylene and the transalkylation of diethylbenzene or diisopropylbenzene with benzene.

U.S. Pat. No. 6,809,055 B2 entitled "Zeolites and Molecular Sieves and the Use Thereof" discloses controlled conditions to remove the organic template in template-containing zeolites to achieve a higher acidity and more active catalyst than the catalyst produced using conditions in existing commercial production of zeolites.

A specially prepared zeolite beta (i.e., high performance zeolite beta), disclosed in the above-mentioned patent application, has the ratio of strong acid sites to weak acid sites greater than 1.0 and is more active than conventional zeolite beta. As a critical step in the preparation of high performance zeolite beta, template removal by mild calcination can be implemented relatively easily at small scale either by spreading the zeolite bed thinner over a tray during calcinations, or using a very slow heating rate combined with high air circulation to minimize formation of "hot spots" in the catalyst bed.

SUMMARY

An aromatic alkylation process is provided herein. The process comprises contacting an aromatic compound with an alkylating agent in the presence of a zeolite beta in a reaction zone under alkylation reaction conditions, wherein said zeolite beta is a high performance zeolite beta possessing a ratio of strong acid sites/weak acid sites greater than 1.

The high performance zeolite beta was found to be far superior to conventional zeolite beta in the aromatics alkylation reaction, such as benzene alkylation with ethylene for ethylbenzene production, and benzene alkylation with propylene for cumene production. While not wishing to be limited to specific reactions, other relevant reactions include alkylation of benzene with butylenes(s), alkylation of benzene with C9 to C14 olefins, alkylation of benzene with alcohol(s), and analogous alkylation of naphthalene(s) with olefins or alcohols. The benzene or naphthalene reagents can also include alkylbenzene or alkylnaphthalene. Representative examples of said alkylbenzene and alkylnaphthalene are methylbenzene (toluene) and methylnaphthalene. Many other aromatics can be employed in this invention, including biphenyl, anthracene, and phenanthrene. Also, heterocyclic analogues of the aforementioned aromatics can also be employed in this invention. Some examples include nitrogen compounds, such as pyridine, quinoline, and picolines; and oxygen compounds, such as furan.

DETAILED DESCRIPTION OF PREFERRED EMBODIMENT (S)

This invention is to apply improved zeolite beta, designated herein as "high performance zeolite beta", to the alkylation of aromatics (e.g., benzene) with various alkylating agents, including but not limiting to olefins, e.g., $C_2$-$C_6$ olefins such as ethylene, propylene, butylenes (1-butene, 2-butene, isobutene), pentenes (e.g., n-pentene), hexenes (e.g., n-hexene), or mixtures thereof (e.g., $C_2/C_3$, $C_3/C_4$, or mixed $C_2$-$C_4$ olefins), $C_2$-$C_6$ alcohols such as isopropanol, butanol, or the mixture of two or more to form the corresponding alkylate or mixed alkylates. In the event that a mixed alkylate product is produced, e.g., a product containing ethylbenzene and/or cumene, and/or butylbenzene, a subsequent fractionation step is employed to separate the alkylate components. Also, the alkylating agent for benzene can be n-$C_9$ to n-$C_{14}$ olefins to produce linear alkylbenzenes.

The alkylation reactor can be a fixed-bed, catalytic distillation reactor, or other types of commonly used reactors. It can be carried out in vapor phase, liquid phase, or mixed vapor/liquid phases.

In addition to fixed-bed reaction, one important process for commercial production of ethylbenzene or cumene is the reactive distillation process, in which the alkylation reaction and product/reactant separation occur simultaneously.

Alkylation reaction conditions are well known and typically include a temperature of from about 100° C. to about 300° C., a pressure of from about 200 psig to about 600 psig, a weight hourly space velocity of from about 0.5 to about 10, and a molar ratio of aromatic compound to alkylating agent of from about 1/1 to about 20/1.

This invention is also advantageous for the transalkylation of polyaromatics which were produced as by products in aromatic alkylation. For example, polyethylbenzenes (e.g., di-ethylbenzenes, tri-ethylbenzenes, tetra-ethylbenzenes, etc.) were produced in benzene alkylation with ethylene, and polyisopropylbenzenes (e.g., di-isopropylbenzenes, tri-isopropylbenzenes, tetra-isopropylbenzenes) in benzene alkylation with propylene. These polyalkylbenzenes can be transalkylated with benzene in the presence of high performance zeolite beta to produce mono-alkylbenzene (e.g. EB or cumene) in a fixed-bed reactor. Typically, transalkylation reaction conditions include a temperature of from about 150° C. to about 300° C., a pressure of from about 150 psig to about 600 psig, a space velocity of from about 1.5 to 10.0 WHSV. The molar ratio of phenyl species to alkyl species can range from 1 to 10.

In accordance with one aspect of the present invention, there is provided a zeolite or molecular sieve that has an increased number of so called "strong acid sites", i.e. sites as measured by the temperature-programmed desorption ("TPD") performed in accordance with Example 3. More particularly, Applicant has found that by increasing the number of strong acid sites, there is provided a substantial increase in catalyst activity.

In another embodiment, the zeolite or molecular sieve has a pore volume greater than 0.7 cm$^3$/g.

In accordance with a preferred embodiment of the present invention, the zeolites or molecular sieve has an Acidity-Activity Index (AAI), i.e., a ratio of strong acid sites to weak acid sites of at least 1.0, preferably at least 1.2, and more preferably at least 1.4, and most preferably at least 1.6 wherein AAI, is the ratio of the total ammonia desorbed from the zeolites or molecular sieve at a temperature above 300° C. (a measure of the strong acid sites) to the total ammonia desorbed from the zeolites or molecular sieve at a temperature below 300° C. (a measure of the weak acid sites) as determined by temperature controlled desorption ("TPD") as performed in accordance with the procedure described in U.S. Pat. No. 6,809,055 B2, Example 3.

More particularly in a preferred embodiment, the zeolite or molecular sieve contains silica and alumina in a silica to alumina molar ratio of 6:1 or higher that is prepared by use of a template or organic directing agent that includes an organic nitrogen compound. As representative examples of zeolites there may be mentioned: beta, TEA-mordenite, MCM-22, MCM-36, MCM-39, MCM-41, MCM-48, PSH-3, ZSM-5, Breck 6, ZSM-12, ZSM-22, ZSM-23, ZSM-35, ZSM-48, SSZ-32, etc. However, the preferred zeolite of the invention is zeolite beta.

In accordance with a further aspect of the present invention, Applicant has found that a zeolite or molecular sieve having an improved catalytic activity may be produced by increasing the strong acid sites thereof. In this respect, Applicant has found that during the procedures for producing zeolites and molecular sieves, and in particular the procedure for removing the organic nitrogen templating agent, the conditions employed therein should be controlled to preserve strong acid sites. In this respect, strong acid sites are maintained by employing process conditions which prevent loss of those sites that are proven to be beneficial in catalytic conversion applications and are be characterized by its AAI ratio. It is believed that those sites can be ascribed to be a specific kind of tetrahedral aluminum sites in the zeolites or molecular sieve structure.

In this respect, in removing the organic nitrogen templating agent (in general, at least 50% thereof is removed, and in a preferred embodiment essentially all is removed), heating is controlled to prevent exposure to average temperatures that are above about 575° C. and preferably the heating is to an average temperature of no greater than 550° C. (in general, at least 50% thereof is removed and in a preferred embodiment essentially all is removed). Moreover, in a preferred embodiment, heating should be controlled so to limit the final calcination temperature. Moreover, the temperature increase of the material is sufficiently slow such that local overheating to temperatures above about 575° C. is prevented and/or minimized.

Furthermore, in one preferred operation the calcination to remove the templating agent is performed in a shallow bed in order to reduce local overheating or the occurrence of hot spots. Alternatively, a deep catalyst bed could be employed if the flowing gas is of sufficiently high superficial velocity such that the heat transfer rate maintains the catalyst bed temperature at any point to no more than about 25° C. difference from the average bed temperature. In yet another method, overheating during the calcination can be minimized by employing intermediate stops in the temperature ramp or to control hot spots by reducing/controlling oxygen flow thereby controlling heating by combustion of the organic directing agent. Other possibilities known in the art may be employed to minimize local overheating or the occurrence of hot spots.

Applicants have further found that steam may affect the catalytic activity of the zeolite or molecular sieve. As a result, in a preferred embodiment, in calcining the zeolite or molecular sieve, the zeolite or molecular sieve is slowly heated to the final calcination temperature. Controlled heating to temperatures up to 300° C., aimed at minimizing exposure to temperatures above 300° C., removes water before high temperatures are reached so as to minimize steaming, and thereby preserve strong acid sites. In one embodiment this can be effected by applying slow heatup rates, such as, for example, less than 10° C./min, preferably less than 5° C./min.

While not wishing to be bound by theory, the current working model to explain cause of the high catalyst activity relates to so-called "strong acid sites". These strong acid sites are reduced primarily as a result of a loss of a specific type of tetrahedral aluminum. As a result, in accordance with an aspect of the present invention, in producing a zeolite or molecular sieve, processing conditions that reduce the amount of the specific type of tetrahedral aluminum and thereby reduce the number of strong acid sites should be minimized or avoided in order to provide for improved catalyst activity. As hereinabove indicated, in order to minimize the loss of the specific tetrahedral aluminum and thereby maintain a certain minimum amount of strong acid sites, the conditions at which the templating agent is removed should be controlled so as to reduce and/or eliminate exposure to temperatures above about 550° C. for a prolonged period of time. In addition, in a preferred embodiment steaming should be avoided; for example, but not limited to, by slow heating to the final calcination temperature.

Moreover, processing of the zeolite or molecular sieve after the removal of the templating agent should also be controlled to reduce and/or eliminate exposure to temperatures above about 550° C. For example, the exchange steps and final calcination of the ion exchanged zeolite or molecular sieve should occur at moderate temperatures. Ion exchange includes, but is not limited to, partial or full exchange of Na with $NH_4NO_3$ to produce the $NH_4$-form of the zeolite or molecular sieve. In addition, use of organic agents in procedures for extruding the zeolites or molecular sieve into a desired shape or form should also be minimized or avoided.

The prior art did not recognize that strong acid sites in zeolites and molecular sieves increase catalytic activity and that processing conditions for producing zeolites and molecular sieves should be controlled to prevent loss of strong acid sites. In the prior art, processing steps after formation of the zeolites or molecular sieve reduced the number of strong acid sites to values below those of the present invention, and such reduction resulted in a reduction in catalytic activity.

The zeolites and molecular sieves of the present invention may be combined with other materials, as known in the art. For example, zeolites and molecular sieves may optionally be metal cation exchanged following the hydrogen-forming cation exchange. If the zeolites and molecular sieves are metal cation exchanged after the hydrogen forming cation exchange, the zeolites or molecular sieve component thereof preferably includes a number of acid sites as hereinabove described. As representatives of metal cations, there may be mentioned cations of Group IIA (Mg, Ca, Sr, Ba), Group IIIA (B, Al, Ga, In), Group IIIB (Sc, Y, and the lanthanide elements), Group IVB (Ti, Zr, Hf), Group VB (V, Nb, Ta), Group VIB (Cr, Mo, W), and Group VIIB (Mn, Tc, Re) of the Periodic Table of the Elements. The use of such metal cations is known in the art, and the incorporation of such additional metal cations and the amount thereof is deemed to be within the skill of the art from the teachings herein. Similarly, the zeolites or molecular sieve may be employed with one or more inorganic oxide matrix components, which is generally combined with zeolites and molecular sieves during the exchange with a metal cation if used. Such matrix components are general inorganic oxides such as silica-aluminas, clays, aluminas, silicas, etc. The matrix may be in the form of a sol, hydrogel or gel and is generally an alumina, silica or silica-alumina component such as a conventional silica-alumina catalyst. The matrix may be catalytically active or inert. In a preferred embodiment, when combined with a matrix, the zeolite or molecular sieve component has a number of strong acid sites, as hereinabove described.

As hereinabove described, in order to maintain strong acid sites, the processing conditions should be controlled to avoid exposing the zeolite or molecular sieve to elevated temperatures for a prolonged period of time.

The "high performance zeolite beta" catalyst was evaluated in the alkylation reaction of benzene with olefins, such as ethylene or propylene, in a re-circulating differential fixed-bed reactor. To feed concentration of 0.32-0.38 wt % ethylene or 0.40-0.45 wt % propylene was pre-dissolved in benzene. 0.50-0.75 grams of catalyst with particle sizes of 12-20 mesh, crushed from extrudates, was loaded in a 7/8" ID SS tube reactor. The feed rate was 6.25 g/min. For EB formation the reactor temperature, pressure, and recirculation rate were normally at 190° C., 350 psig, and 200 gram/min, respectively. For cumene formation the reactor temperature, pressure, and recirculation rate were normally at 170° C., 300 psig, and 200 gram/min, respectively. The products were analyzed by GC equipped with DB-Wax 30 m, 0.25 mm ID capillary column and flame detector.

The catalyst activity was expressed in specific reaction rate constant with an assumption of $1^{st}$ order reaction kinetics. Catalyst selectivity can be gauged from the key byproducts, such as Diethylbenzene/EB ratio for EB synthesis, and n-Propylbenzene (nPB) and Di-isopropylbenzene (DIPB) for cumene synthesis.

The following examples illustrate the process of the invention using high performance zeolite beta catalyst as opposed to use of conventional catalysts as illustrated in the comparison examples.

EXAMPLES AND COMPARATIVE EXAMPLES

Example 1 and Comparative Examples 2 and 3

In Example 1 and Comparative Examples 2 and 3, benzene alkylation with ethylene to form ethylbenzene was performed according to the method described above. In Example 1 the catalyst of the invention "high performance beta" was employed in the alkylation process. In Comparative Examples 2 and 3, conventional zeolite beta from two different sources were used. Table 1 below summarizes the test results of the high performance zeolite beta and two conventional zeolite betas. Compared to the two commercial zeolite beta, the high performance zeolite beta is two times more active. Formation of key byproducts, such as diethyl benzene (DEB), is comparable among different zeolite beta catalysts given the fluctuation of DEB/EB was around 0.001 due to the variation of ethylene concentration in the feed.

TABLE 1

Test results of different zeolite beta in benzene alkylation with ethylene

| | Example 1 High performance beta | Comp. Example 2 Conventional beta I | Comp. Example 3 Conventional beta II |
|---|---|---|---|
| Activity ($k_{eb}$) ($cm^3\ C_2^-$/s-g) | 0.76 | 0.38 | 0.34 |
| Key Byproduct DEB/EB (w/w) | 0.008 | 0.0075 | 0.008 |

Notes:
Zeolite beta I and II were obtained from two different commercial manufacturers.

Example 4 and Comparative Examples 5 and 6

In Example 4 and Comparative Examples 5 and 6, benzene alkylation with propylene to form cumene was performed according to the method described above. In Example 4 the catalyst of the invention "high performance beta" was employed in the alkylation process. In Comparative Examples 5 and 6, conventional zeolite beta and conventional zeolite Y, respectively, were used. Table 2 summarized the test results of high performance zeolite beta, conventional beta and zeolite Y.

Compared to commercial catalysts, high performance zeolite beta is 70% more active than conventional beta and 25% more active than zeolite Y. Formation of key byproducts, such as nPB and DIPB, are slightly lower in our high performance zeolite beta than conventional zeolite beta. However, the amount of DIPB formed using conventional zeolite Y is three times more than the beta catalysts. Therefore, zeolite Y is much less selective than zeolite beta to the desired product of mono-alkylated benzene (cumene).

TABLE 2

Test results of different zeolite catalysts in
benzene alkylation with propylene

|  | Example 4 High performance beta | Comp. Example 5 Conventional beta | Comp. Example 6 Conventional Y |
|---|---|---|---|
| Activity ($cm^3$ $C_3^=$/s-g) | 1.97 | 1.16 | 1.58 |
| Key By-products* |  |  |  |
| n-PB (ppm) | 276 | 298 | 224 |
| DIPB (wt %) | 0.45 | 0.53 | 1.63 |

*n-PB = n-Propylbenzene, DIPB = Di-isopropylbenzene

Example 7 and Comparative Example 8

In Example 7 and Comparative Example 8 polyalkylated aromatic compounds were transalkylated with benzene to produce the monoalkylated compound. Testing was carried out in the fixed bed reactor in liquid phase, up-flow mode. 30 Grams of catalyst were loaded in a ⅞" ID SS tube reactor in "as is" extrudate form. The feed is a mixture of benzene (Bz) and di-ethylbenzene (DEB) with a molar ratio of Bz/DEB of 2.3. The DEB was a mixture of different isomers, including 1,3-DEB (64.4%), 1,4-DEB (29.6%) and 1,2-DEB (4.1%). The catalyst was washed prior to the test by hot benzene at 204° C. for 6 hours with reactor pressure set at 300 psig. During the test the reactor temperature and pressure were controlled at 204° C. and 300 psig, respectively, with WHSV of 4.

The feed or product sample was analyzed by GC equipped with a capillary column (DB-160 m, 0.25 mm ID) with a flame detector. The test results are set forth below in Table 3.

TABLE 3

Test results of different zeolite beta in transalkylation reaction

|  | Example 7 High performance beta | Comp. Example 8 Conventional beta I |
|---|---|---|
| Total DEB Convention (%) | 36.5 | 11.9 |
| Ethylbenzene in Product (wt %) | 24.7 | 7.6 |

It is clear from the results above that the high performance zeolite beta of the invention is much more superior than conventional beta in both activity and EB yield. High performance zeolite beta is three times more active than conventional zeolite beta.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. An aromatic alkylation process comprising:
   contacting an aromatic compound with at least one alkylating agent in the presence of a zeolite beta catalyst in a reaction zone under alkylation reaction conditions to provide a product containing at least one alkylate, wherein said zeolite beta possesses a ratio of strong acid sites/weak acid sites greater than 1.

2. The process of claim 1 wherein the aromatic compound is selected from the group consisting of benzene, alkylated benzene, naphthalene and alkylated naphthalene.

3. The process of claim 1 wherein the alkylating agent comprises at least one compound from the group of $C_2$ to $C_6$ olefins.

4. The process of claim 1 wherein the alkylating agent is ethylene.

5. The process of claim 1 wherein the alkylating agent is propylene.

6. The process of claim 1 wherein the alkylating agent is a butylene.

7. The process of claim 1 wherein the alkylating agent is n-hexene.

8. The process of claim 1 wherein the alkylating agent is an n-$C_9$ to n-$C_{14}$ olefin.

9. The process of claim 1 wherein the contents of the aromatic compound and alkylating agent are in the gas phase.

10. The process of claim 1 wherein the contents of the aromatic compound and alkylating agent are in the liquid phase.

11. The process of claim 1 wherein the contents of the aromatic compound and alkylating agent are in the mixed gas-liquid phases.

12. The process of claim 1, wherein the aromatic compound is benzene, the alkylating agent is ethylene and the alkylation is carried out with a benzene/ethylene molar ratio of 1 to 5.

13. The process of claim 1 wherein the zeolite beta has a ratio of strong acid to weak acid sites of at least 1.2.

14. The process of claim 1 wherein the zeolite beta has a ratio of strong acid to weak acid sites of at least 1.4.

15. The process of claim 1 wherein the zeolite beta has a ratio of strong acid to weak acid sites of at least 1.6.

16. The process of claim 1 wherein the zeolite beta has a pore volume greater than 0.7 $cm^3$/g.

17. The process of claim 1 wherein the at least one alkylating agent comprises a mixed olefin stream containing at least two olefins selected from the group consisting of ethylene, propylene, butene, 2-butene and isobutylene, and the process further includes a fractionation step for separating mixed alkylated products.

18. The process of claim 1 wherein the alkylation reaction conditions include a temperature of from about 100° C., to about 300° C., a pressure of from about 30 psig to about 600 psig, and a weight hourly space velocity of from about 0.5 to about 10.

* * * * *